United States Patent [19]

Sakazume et al.

[11] Patent Number: 5,770,461
[45] Date of Patent: Jun. 23, 1998

[54] METHOD AND APPARATUS FOR SEPARATION OF SOLID SUPPORTS AND LIQUID PHASE

[75] Inventors: Taku Sakazume; Kyoko Imai, both of Hitachinaka; Yasushi Nomura, Mito, all of Japan

[73] Assignee: Hitachi, Ltd., Tokyo, Japan

[21] Appl. No.: 520,781

[22] Filed: Aug. 30, 1995

[30] Foreign Application Priority Data

Sep. 2, 1994 [JP] Japan .................................. 6-209893

[51] Int. Cl.⁶ ................................................ G01N 33/553
[52] U.S. Cl. .................. 436/526; 435/283.1; 435/287.2; 435/287.9; 436/806; 436/824; 209/5; 209/214; 210/222; 210/695
[58] Field of Search ............................. 435/283.1, 287.2, 435/287.9; 436/526, 806, 824; 209/5, 214; 210/222, 695

[56] References Cited

U.S. PATENT DOCUMENTS 5,318,914  6/1994  Matte et al. ............................ 436/526

FOREIGN PATENT DOCUMENTS 51-64       1/1976   Japan .
63-210773   9/1988   Japan .
1-45579    10/1989   Japan .
2-161358    6/1990   Japan .

*Primary Examiner*—Susan Wolski
*Attorney, Agent, or Firm*—Fay, Sharpe, Beall, Fagan, Minnich & McKee

[57] ABSTRACT

A method and apparatus for separating solid supports formed of magnetic particles on which immunocomplexes are bound, from a liquid phase includes a reaction container containing a fluid in which magnetic particles having immunocomplex bound thereon are suspended. The reaction container is positioned at a flock forming station, where the fluid is subjected to an alternate current magnetic field having a temporally varying intensity by an electromagnetic. The magnetic particles are flocculated with each other due to the application of such varying magnetic field to form a multiplicity of flocks. A stronger magnetic field then is applied to the resulting contents in the reaction container by a permanent magnet. The flocks are magnetically fixed on the inner wall surface of the reaction container by the action of the stronger magnetic field. While the magnetic particles are being fixed on the inner wall surface, a nozzle is inserted into the reaction container to suck the unnecessary liquid phase and remove it from the reaction container.

8 Claims, 6 Drawing Sheets

METHOD AND APPARATUS FOR SEPARATION OF SOLID SUPPORTS AND LIQUID PHASE

BACKGROUND OF THE INVENTION

The present invention relates to a method and apparatus for separating solid supports and a liquid phase, and more particularly to such a method and apparatus suitable for immunoassay which employs magnetic particles as solid supports.

JP-B-1-45579 describes that antigens or antibodies in a biological sample are bound onto the surfaces of water insoluble carrier particles to form immunocomplex. For applying such a method to immunoassay, in addition to employing an appropriate labeling agent, a B-F separation process is required to separate a bound phase and a free phase in course of analytical manipulations.

JP-A-2-161358 teaches a method of performing the B-F separation using magnetic particles. More specifically, this prior art binds antigens in samples onto magnetic particles, on which antibodies are immobilized, in a reaction container by a competitive immunoreaction or a sandwich immunoreaction, thereafter applies a magnetic field to attract the magnetic particles onto the inner wall surface of the reaction container, and sucks a free phase in the reaction container for removal, thus achieving the B-F separation.

JP-A-63-210773, on the other hand, describes a method of utilizing magnetic particles having immobilized thereon a substance which is specifically bound to a substance under measurement for promoting a reaction. In this prior art, a liquid in which the magnetic particles are suspended is irradiated with light to measure scattered light from the liquid. In JP-A-63-210773, the magnetic particles and the sample are contained in a container in a suspended state prior to a measurement, and a magnetic field is applied to the suspension to promote a reaction of the substance to be measured in the sample with the substance immobilized on the magnetic particles. This prior art features that the measurement is performed with the magnetic particle being suspended in a container without performing the B-F separation.

For promoting a reaction of magnetic particles serving as solid supports with a substance to be measured in a sample, the magnetic particles preferably hold a dispersed state in a liquid. For this purpose, the magnetic particles are composed of a synthetic resin and a magnetic material, and the specific gravity of the magnetic particles is adjusted by varying the composition ratio of these two components.

However, since magnetic particles used in immunoassay are micro particles having a diameter of 1–2 μm, a sufficient recovery ratio is not achieved for such magnetic micro particles captured by a magnet on the inner wall surface of the container during the B-F separation, and part of the magnetic micro particles are lost when the free phase is sucked and removed from the container. This low recovery ratio for the magnetic micro particles results in less accurate analysis and measurement.

SUMMARY OF THE INVENTION

It is an object of the present invention to provide a method and apparatus which prevent a part of a bound phase from being lost during removal of a free phase during the B-F separation.

It is another object of the present invention to provide a method and apparatus which can reliably and rapidly carry out the B-F separation.

It is a further object of the present invention to provide a method and apparatus which can eliminate interfering substances unspecifically attached to solid supports by once magnetically fixing the solid supports having immunocomplex bound thereto on the inner wall surface of a container and then sufficiently suspending the solid supports again in a washing liquid.

In the present invention, prior to the separation of a bound phase and a free phase, magnetic micro particles having immobilized thereon a substance to be specifically bound with a substance to be measured and the substance to be measured in a sample are subjected to immunoreaction to form immunocomplex on the magnetic particles. A magnetic field is applied from the outside of a container containing a fluid including solid supports formed of the magnetic particles and the free phase, such that a varying magnetic field generating repetitive magnetic displacement of the solid supports is applied to the fluid. The application of the magnetic field allows the solid supports to form flocculation in a suspended state. Then, a fixed strong magnetic field is applied to the fluid, in which the flocculation has been formed, for magnetically fixing the solid supports on the inner wall surface of the container, and then the free phase is sucked and removed from the container while the solid supports are fixed.

When a washing liquid is fed to the container in which the first B-F separation has been completed and the application of the magnetic field is stopped, the solid supports are dispersed into the washing liquid. By employing a magnetic material exhibiting small residual magnetism as the magnetic material included in the magnetic particles, individual magnetic particles are scatteringly dispersed into the washing liquid when the application of the magnetic field is stopped. In this way, interfering substances possibly attached to the flocks of the magnetic particles are eluded into the washing liquid.

Preferably, prior to the step of applying the varying magnetic field for generating the magnetic displacement, a substance for promoting the flocculation is added to the fluid. A typical example of such promotor substances is magnetic particles having a relatively large diameter in the range of 10–50 μm. Antigens or antibodies need not be immobilized on the surfaces of these large magnetic particles. On the other hand, the magnetic particles for immunoassay have a diameter of 1–2 μm.

Means for applying the magnetic field for magnetically fixing the solid supports preferably includes a permanent magnet, and particularly, a magnet made of an element belonging to the rare earth group is suitable.

When the solid supports are flocculated to form flocks and those flocks are magnetically collected, larger magnetic forces acting on the magnetic particles and thus faster collecting speed are achieved than the case where the individual solid supports are magnetically collected as they are without forming flocks. Further, since individual magnetic particles are sharply decreased because of the formation of flocks, the solid supports are more likely to be firmly fixed on the inner wall surface of the container. Thus, the number of magnetic particles discharged together with the free phase is largely reduced.

When a strong magnetic field is applied to a magnetic particle suspended liquid, the magnetic particles cause translational motion in accordance with the product of the magnetic flux density of the applied magnetic field and its positional gradient. On the other hand, when a weak magnetic field is applied to the particle suspended liquid, the magnetic particles receive torques from the magnetic field to cause rotational motion about their respective centroids.

As the magnetic micro particles are flocculated to form flocks of larger volumes, forces magnetically acting on the flocks increase. By applying a temporally varying magnetic field, repetitive magnetic displacement of the magnetic micro particles (rotational motion and translational motion) is generated, so that opportunities of the magnetic micro particles coming in contact with each other in the magnetic field are remarkably increased, and flocks of the magnetic micro particles are produced. As described above, when the magnetic micro particles are collected in the form of flocks, larger magnetic forces acting on the magnetic particles and thus a higher collecting efficiency are achieved than when they are individually collected.

Further, when the magnetic micro particles are magnetically displaced repetitively, the magnetic micro particles are given motion different from simple agitating motion for dispersing them in a liquid. This motion effectively shakes down substances unspecifically adsorbed on the solid support particles, thus promoting the elusion of such substances into the washing liquid.

DESCRIPTION OF THE PREFERRED EMBODIMENTS

A first embodiment of the present invention will hereinafter be described with reference to FIGS. 1–5. An analyzer shown in FIG. 1 performs a non-competitive immunoassay called a sandwich method. On a holder 2, a multiplicity of reaction containers 1 are arranged in a circle to form a reaction line by these reaction containers 1. The holder 2 functions as a container carrier and comprises a donut-like turn table which is intermittently driven by a pinion gear 4.

Figure 1:
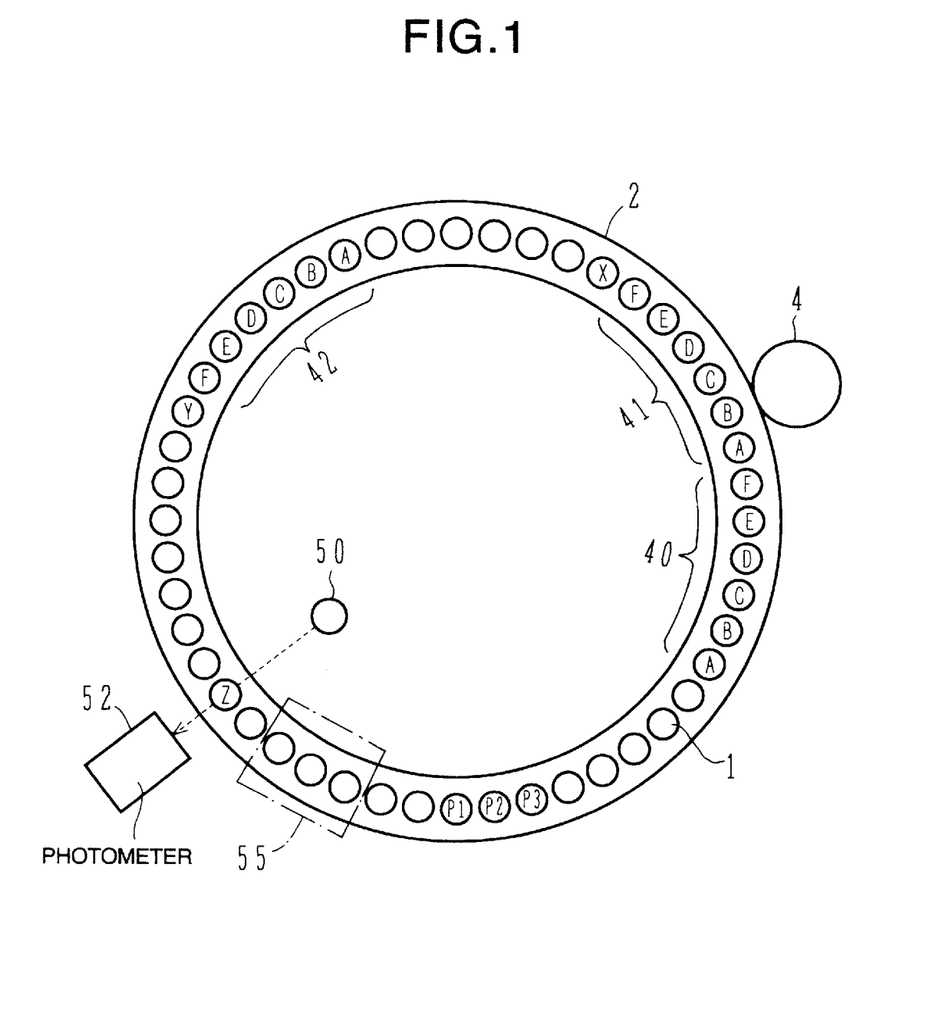
FIG. 1 is a schematic diagram for explaining a reaction line of an automated immunoassay analyzer to which the present invention is applied.

At a position P1, a reaction container 1 is fed with a predetermined amount of a biological sample including a substance to be measured by a pipette unit, not shown. Then, at a subsequent position P2, the reaction container 1 is also fed with a predetermined amount of buffer solution. Next, at a position P3, the reaction container 1 is further fed with a predetermined amount of solution including magnetic micro particles serving as solid supports. The magnetic micro particles have immobilized on the surfaces thereof an antibody which is capable of a specific binding reaction with the substance to be measured. The content in the reaction container 1 is then incubated, and an immunoreaction progresses such that the antibody immobilized on the magnetic particles and an antigen in the sample form an immunocomplex. This reaction causes the substance to be measured to be bound to the magnetic particles.

The reaction container 1 including a solution having the immunocomplex formed therein is next transported to a B-F separation processing station 40. Details of the B-F separation processing will be described later. By the B-F separation, a bound component remains in the reaction container 1, while a free component is removed from the reaction container 1 by a sucking means. Next, the bound component is treated three times with a washing operation including a B-F separation. However, FIG. 1 only shows one washing station 41 for simplification of the drawing.

The reaction container 1 including the washed bound component is treated at a position X with a predetermined amount of reagent solution including an enzyme labeled antibody. During incubation, an immunoreaction progresses wherein the labeled antibody is bound to the antigen bound on the magnetic particles. By a subsequent B-F separation in a station 42, the bound component including the antigen to be measured and the labeled antibody bound on the magnetic micro particles is left in the reaction container 1, while the free phase including a non-reacted reagent is sucked and removed from the reaction container 1. Afterward, a washing process including a B-F separation is repeated three times on the bound component. It should be noted that stations for performing those washing operations are not shown in FIG. 1 for simplification of the drawing.

Subsequently, the reaction container 1 is fed with a substrate solution, and an enzyme reaction progresses during incubation. The reaction container 1 including the reactive solution is irradiated with a light beam from a light source 50 at a position z, and the light through the reaction container 1 is received by a photometer 52 including a spectroscope. The concentration of the substance to be measured in the sample is calculated based on a detection signal generated by the photometer 52.

The reaction container 1, after the measurement, is washed by a washing liquid in a container washing station 55 such that no solid supports remain therein. After removing the washing liquid, the washed reaction container 1 is again utilized for a subsequent analysis.

Figure 2:
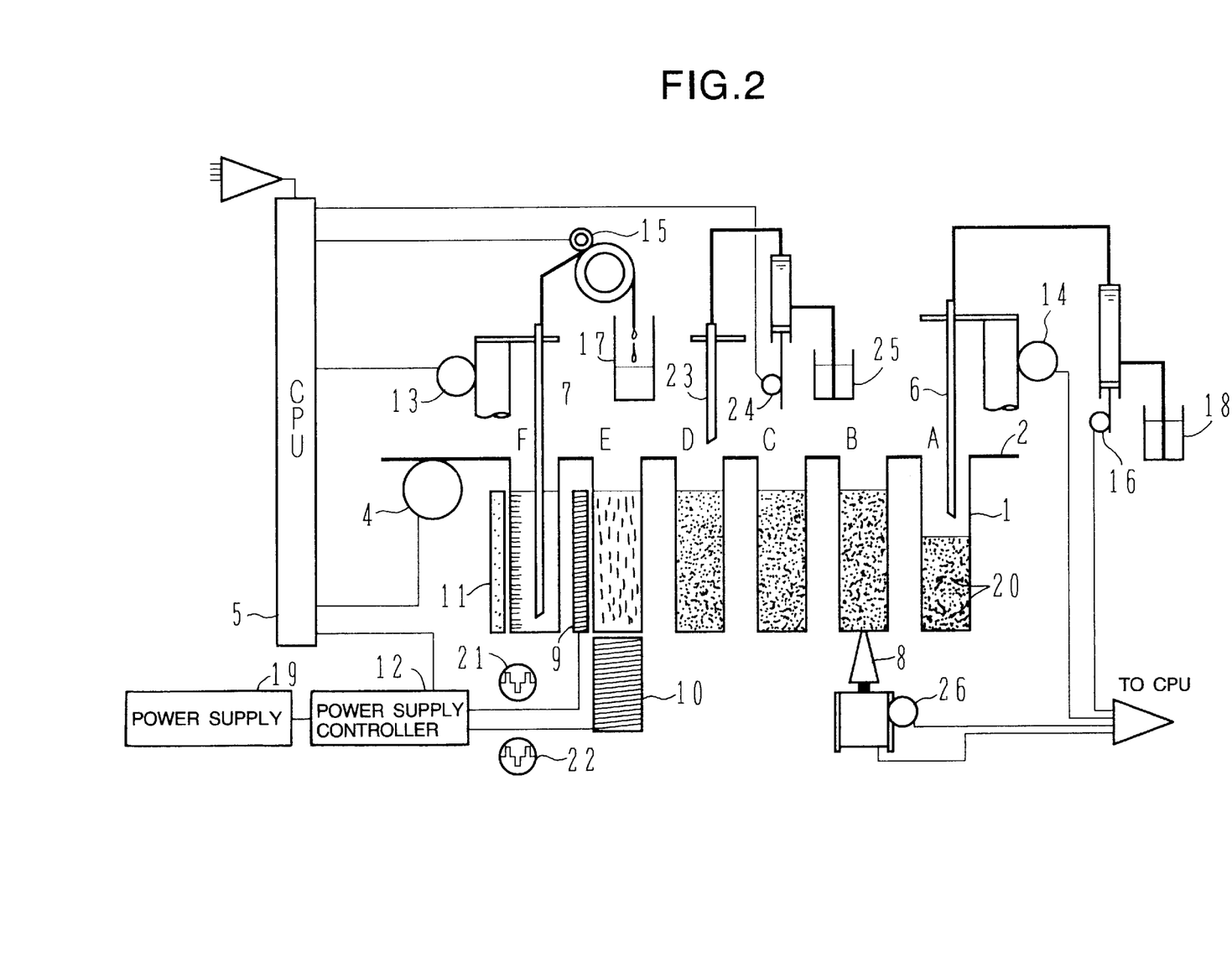
FIG. 2 is a diagram illustrating B-F separation processing in the analyzer shown in FIG. 1.
Figure 3:
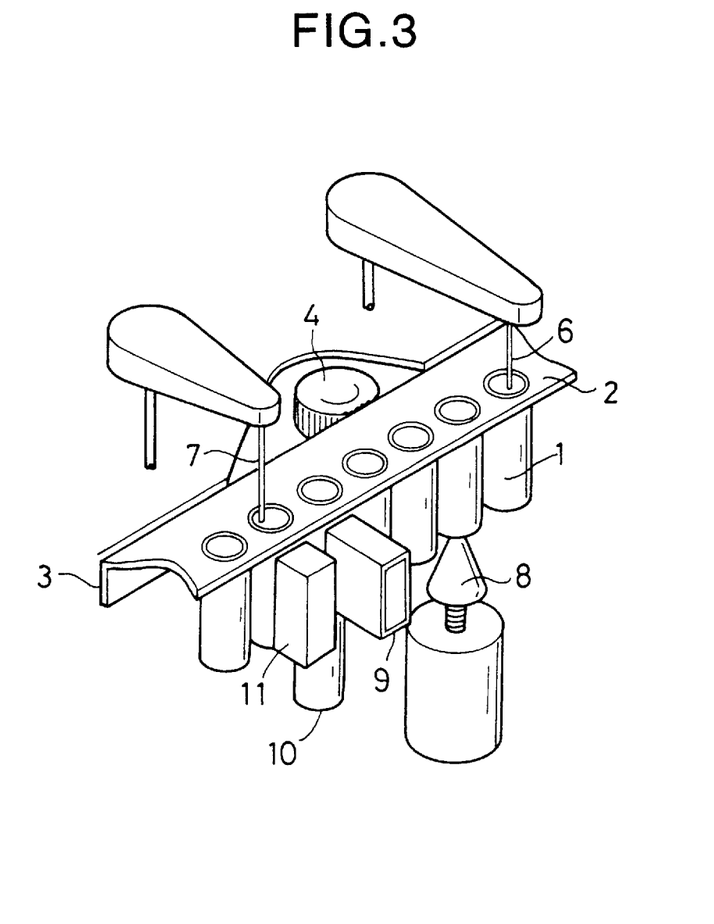
FIG. 3 is a schematic perspective view illustrating an outer appearance including a main portion of the analyzer shown in FIG. 2.

FIG. 2 illustrates only a set of steps for implementing the B-F separation in the stations 40, 41, 42 shown in FIG. 1. It should be noted that the analyzer of FIG. 1 is provided with a plurality of sets of like configurations. As illustrated in greater detail in FIG. 3, the holder 2 is provided with a rack 3 on a side edge thereof and a rotating force of the pinion 4 is transmitted to the holder 2 through the rack 3.

The pinion 4 of the transportation system is controlled by a signal from a controller 5. In this case, the reaction containers 1 are stopped for a fixed time period in an intermittent transportation thereof for performing respective steps, later described, by respective mechanisms disposed along the reaction container line, and then the reaction containers 1 are transported to be positioned to respective different positions. These intermittent stop and transportation operations are repeated during the analysis.

Referring specifically to FIG. 2, first, when a reaction container 1 is positioned at a position A at a first timing, a nozzle 6 is lowered by an up-and-down mechanism 14 to feed the reaction container 1 with a washing liquid prepared in a washing liquid tank 18 through the nozzle 6. If the reaction container 1 has been already filled, an extra portion of the washing liquid required for washing may be added in the reaction container 1. The amount of washing liquid is controlled by the controller 5 through a syringe 16 every time the washing liquid is fed to a different reaction container 1. The up-and-down mechanism 14 is also controlled by a signal from the controller 5. Several kinds of washing liquid may be provided such that a suitable one is selected therefrom in accordance with a particular washing process and a substance to be washed.

The reaction container 1 is next positioned at a position B at a second timing. At the position B, the reaction container 1 is oscillated for agitation by an agitator mechanism 8 disposed below the holder 2 by bringing the agitator mechanism 8 into contact with the bottom of the reaction container 1 by an up-and-down mechanism 26 at a timing at which the agitation is required. This agitation causes the washing liquid to be sufficiently mixed with the magnetic micro particles 20 as solid supports to disperse the particles which have been flocculated by a magnetic action, so as to sufficiently elude into the washing liquid substances adsorbed on the magnetic micro particles 20 as solid supports not by an immunological specific binding but in an unspecific manner. The operations of the agitator mechanism 8 and the up-and-down mechanism 26 are also controlled by signals from the controller 5. Instead of the agitator mechanism 8 in FIG. 2, an agitating method which employs an ultrasonic device or the like in contact with the reaction container 1 is also effective.

At a third timing at the position C, a suspension including the magnetic micro particles is left as it is. At a position D at a fourth timing, a nozzle 23 feeds the reaction container 1 with a flocculent contained in a tank 25 for promoting flocculation of the magnetic micro particles. By operating a syringe 24 based on instructions from the controller 5, a predetermined amount of the flocculent is discharged from the nozzle 23 into the reaction container 1.

The flocculent added to the reaction container 1 may be magnetic micro particles which exhibit a good responsibility to magnetism. For example, particles having a relatively large diameter ranging from 10 to 50 $\mu$m and exhibiting an excellent responsibility to magnetism, which have been processed to prevent specific binding are added in the washing liquid by the nozzle 6. By thus adding large diameter particles excellent in magnetic response, when a magnetic displacement is repetitively applied to the magnetic particles in the reaction container 1 in a latter stage at a position E, the flocculation takes place with the particles functioning as nuclei, and consequently the flock producing speed is enhanced.

Alternatively, a multi-valent cation (cation having two-valent or a number of valent more than two, or a material generally referred to as a flocculation promotor) may also be used as the flocculent. This agent may be used independently or together with the foregoing magnetic micro particles excellent in magnetic response.

At a fifth timing, the reaction container 1 is positioned at a position E. At the position E, a horizontal coil 9 and a vertical coil 10 are disposed for generating orthogonal magnetic fields for the liquid in the reaction container 1. These coils 9, 10 are respectively applied from a power supply controller 12 with temporally varying currents independently of each other, such as periodically varying pulse currents designated at 21, 22 to generate temporally varying magnetic fields. The power supply controller 12 controls a power supply 19 in accordance with signals generated from the controller 5 to generate the temporally varying currents 21, 22.

Since the magnetic fields generated by the coils 9, 10 depend on currents, and the resistance values of the coils are likely to change due to heat generated by the coils, the magnetic fields are desirably controlled by currents in this embodiment. Both the pulse currents 21, 22 may have a period (a pitch of one pulse) of approximately one second, for example.

By applying to the reaction container 1 the temporally varying magnetic fields generated by the coils 9, 10 as described above, the magnetic micro particles contained in the reactive container 1 are magnetically repetitively displaced, so that the magnetic micro particles as solid supports dispersed in the liquid are flocculated to produce a large number of flocks of the magnetic micro particles.

Subsequently, when the reaction container 1 is positioned at a position F at a sixth timing, the magnetic micro particle flocks flocculated as described above are magnetically adsorbed and fixed onto the inner wall surface or inner bottom surface of the reaction container 1 by a magnetic force of a permanent magnet 11. After the magnetic micro particle flocks are firmly fixed, a suction nozzle 7 is lowered by an up-and-down mechanism 13. The tip of the nozzle 7 is dipped into the liquid in the reaction container 1, and then driven by a pump 15 to suck the liquid in the reaction container 1 such that all the liquid phase is substantially completely removed therefrom. After the liquid phase has been removed, the nozzle 7 is raised above the reaction container 1. The waste liquid thus sucked from the reaction container 1 is collected in a tank 17. The operations of the up-and-down mechanism 13 and the pump 15 are controlled by the controller 5.

A sequence of steps at the positions A - E are performed for the separation of the bound phase and the free phase in the reactive liquid in the stations 40, 42, and also for the separation of the solid supports dispersed in the washing liquid from a waste liquid during the washing operation in the station 41 shown in FIG. 1.

The second and subsequent washing operations in the washing stations now shown in FIG. 1 are also performed in the above described manner on the reaction container positioned at the positions A - E in order to elude substances unspecifically adsorbed on the solid supports (magnetic micro particles), which were not completely removed by the first washing operation, into the washing liquid for removing such substances.

Next, the flocculation action of the magnetic micro particles at the position E will be described with reference to FIGS. 4A to 4C and 5.

Figure 4A:
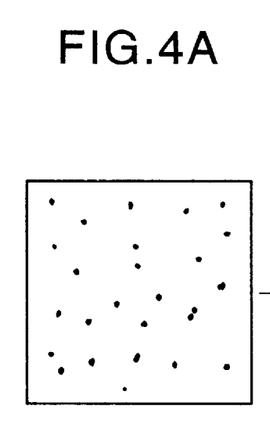
FIGS. 4A–4C are diagrams for explaining how flocculation progresses.
Figure 4B:
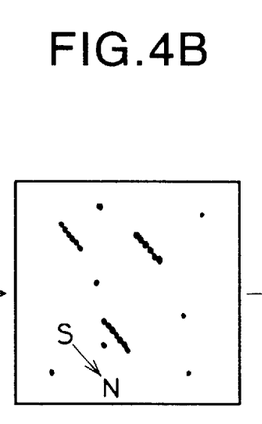
Figure 4C:
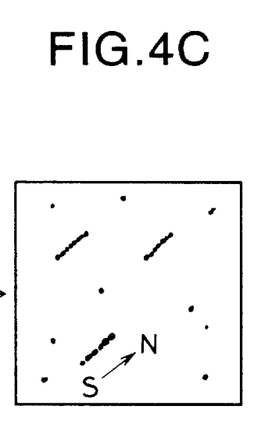

First, as shown in FIG. 4A, when a magnetic field is applied to magnetize magnetic micro particles dispersed in a liquid, individual magnetic micro particles are gradually associated with each other in a rope form in accordance with the direction of the magnetic field, as shown in FIG. 4B. Then, when a magnetic field is applied to the elongated magnetic micro particle flocks thus associated in a rope form in a direction different from the longitudinal direction thereof, the rope-like magnetic micro particle flocks rotate to direct to the same direction as the direction of the magnetic field, as shown in FIG. 4C. An extremely weak magnetic field is sufficient to cause this rotation. When a stronger magnetic field is further applied, the rope-like magnetic micro particle flocks cause translational motion along the direction of the magnetic field against the viscous resistance of the liquid. In this event, the moving speeds of the respective magnetic micro particle flocks are proportional to the intensity of the magnetic field and the sizes of the respective flocks. More specifically, the magnetic micro particle flocks move faster as the magnetic field is stronger or as the magnetic micro particle flocks are larger. For this reason, when a magnet is employed for adsorption, larger particle flocks only are adsorbed, while smaller particle flocks slowly move later.

Figure 5:
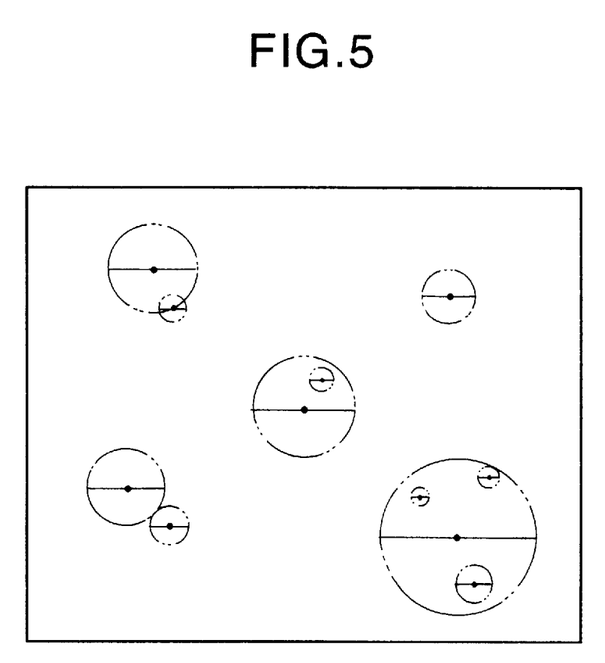
FIG. 5 is a diagram for explaining the formation of flocks of magnetic micro particles.

At the position E, the horizontal coil 9 and the vertical coil 10 are employed to flocculate the magnetic micro particles based on the foregoing principles. More specifically, when a pulse current such as the current 21 is applied to the horizontal coil 9 to generate a temporally varying magnetic field in the reaction container 1, the magnetic micro particles are associated with each other in a rope form in accordance with the direction of the magnetic field to form elongated magnetic micro particle flocks. The direction of the magnetic field changes by 180° in response to the pulse shape of the current 21. This change in the direction of the magnetic field provides each elongated magnetic micro particle flock with a torque, so that each elongated magnetic micro particle flock is rotated about its centroid by 180°. FIG. 5 illustrates this 180° rotation of several magnetic micro particle flocks. When an elongated magnetic micro particle flock is rotated, magnetic micro particles and smaller magnetic micro particle flocks existing within an area traced by the rotation of the elongated magnetic micro particle flock are merged or adsorbed by the elongated magnetic micro particle flock. In this way, the elongated magnetic micro particle flock grows larger. As a particle flock becomes larger, the magnetic field exerts a larger force on the particle flock, thus causing translational motion as well as the rotational motion to the particle flock. This translational motion allows the particle flock to successively come in contact with magnetic micro particles and smaller magnetic micro particle flocks even out of its rotating range and to merge them to transform itself to a larger flock.

Additionally, when the vertical coil 10 applies a temporally varying magnetic field in a direction different from the direction of the magnetic field generated by the horizontal coil 9, i.e., in the direction orthogonal to the surface of the drawing in this case, similar phenomena take place in this direction, resulting in three-dimensional association and displacement of magnetic micro particles and consequently three-dimensional flocculation.

It should be noted here that the intensities of the magnetic fields generated by the coils 9, 10 should be adjusted in terms of the viscosity of a liquid in the reaction container 1, the size of the reaction container 1, the properties of employed magnetic micro particles, and so on. The intensity of the magnetic field must be high enough to cause displacement of magnetic micro particles only with the application of at least one pulse to the coil. While the horizontal coil 9 is disposed only on one side of the reaction container in FIG. 2, such horizontal coils may be disposed on both sides of the reaction container for synchronously generating magnetic fields from the two horizontal coils.

As described above, by applying temporally varying magnetic fields by the coils 9, 10, magnetic micro particles are mutually flocculated in the magnetic fields. As the flocculation of the magnetic micro particles progresses, magnetic moment generated by the magnetic fields and acting on the magnetic particles and flocks becomes larger due to increased volumes of magnetic particle flocks. Thus, the magnetic particles and flocks acutely react even to a weak magnetic field. Thus, magnetic micro particles are displaced to cause rotational motion about their respective centroids with a weak magnetic field and translational motion toward the magnetic field generating coil with a stronger magnetic field. When the magnetic particles 20 are flocculated to be larger flocks having a more acute responsibility to the magnetic field in the washing liquid, these flocks are correspondingly more likely to come into contact with other particles and thus flocks grow far larger.

By flocculating the magnetic micro particles at the position E as described above, when the flocculated magnetic micro particles or flocks are adsorbed by the permanent magnet 11 at the position F for separation thereof from the liquid, larger forces act on magnetic micro particles forming flocks, so that the micro particles (solid supports) can be separated and recovered at a higher speed. Smaller micro particles, which cannot be individually recovered due to insufficient forces exerting on them, can also be recovered as flocks, so that the micro particle recovery coefficient is remarkably improved. This enables prompt recovery of solid supports and high speed processing in a highly sensitive analysis method employing micro particles on the order of micron to submicron. Further, it is possible to improve a residue ratio of solid supports and enhance the accuracy of the analysis using the micro particles, as compared with the prior art.

Also, when the magnetic micro particles are repetitively magnetically displaced as described above, an additional effect may be expected to shake down substances unspecifically adsorbed on the magnetic micro particles, thus promoting elusion of such substances into a washing liquid. This additional effect contributes to elude analysis interfering substances unspecifically adsorbed on solid supports (micro particles) into a reactive liquid or washing liquid, so that a further improvement on the measurement accuracy is achieved.

A magnetic material for the particles forming solid supports should be selected from magnetic materials which exhibit small residual magnetism. Such magnetic materials with small residual magnetism include so-called soft magnetic materials having a component such as Mn-Zn ferrite, Ni-Zn ferrite, or the like, and micro particles having ultra-magnetism. The ultra-magnetism refers to a property of the magnetic material which exhibits very small residual magnetism appearing when the magnetic material is atomized to the level of magnetic domains (approximately 1 nm), and a micro particle having the ultra-magnetism property refers to a micro particle which includes such particles as part or entirety of its components.

By employing the magnetic material exhibiting small residual magnetism for the magnetic micro particles of the present invention, the magnetic micro particles are magnetized to produce flocks of the magnetic micro particles when a magnetic field is applied thereto at the position E, and they can be magnetically recovered promptly at the position F. On the other hand, since removal of the magnetic field causes magnetism to disappear from the magnetic micro particles, the flocks can be easily separated again into the particles. For this reason, in the second and subsequent washing operations, the flocks can be easily separated again into the magnetic micro particle in the processes at the positions A - D, so that the magnetic micro particles are sufficiently dispersed in the washing liquid.

Next, a second embodiment of the present invention will be described with reference to FIG. 6. In the foregoing embodiment, electromagnets (coils) are employed as means for applying temporally varying magnetic fields for flocculating magnetic micro particles. Alternatively, the present embodiment employs permanent magnets instead of electromagnets, and reaction containers are moved relative to the permanent magnets to apply temporally varying magnetic fields.

Figure 6:
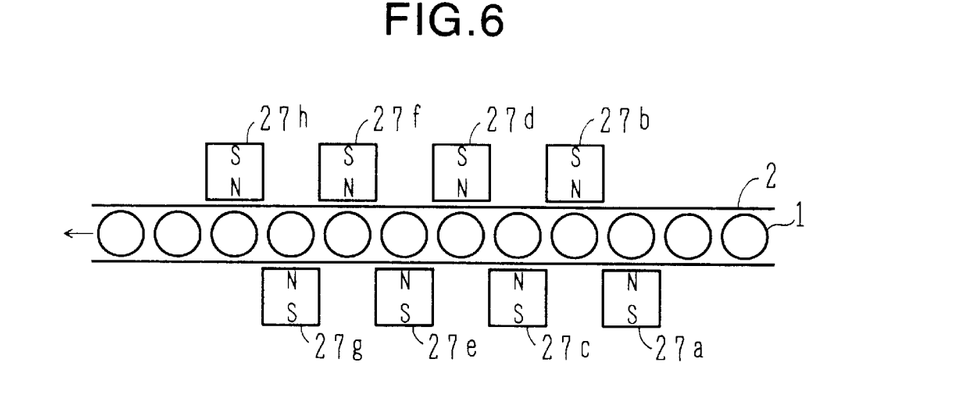
FIG. 6 is a diagram illustrating the configuration for applying a magnetic field according to a second embodiment of the present invention.

Referring specifically to FIG. 6, on both sides of a reaction container holder 2 for transporting reaction containers 1, a plurality of permanent magnets 27a–27h are disposed to sandwich the reaction containers 1. Namely, the permanent magnets 27a–27h are positioned alternately so that they do not face each other. Also, the permanent magnets 27a–27h have the same pole (for example, N-pole) directed to the reaction containers 1. The reaction containers 1 are transported between these permanent magnets in one direction. As the reaction container 1 is transported relative to the permanent magnets 27a–27h disposed on both sides of the holder 2, magnetic micro particles in the reaction container 1 are applied with magnetic fields which change their directions over time. By the action of the permanent magnets 27a–27h, the magnetic micro particles are repetitively magnetically displaced or rotated to form flocks. More specifically, while the reaction container 1 is moved from a position facing the permanent magnet 27a to a position facing the permanent magnet 27b, the direction of the magnetic field applied to the reaction container 1 changes by 180°. This change in the direction of the magnetic field causes the magnetic micro particles to rotate by 180° about their respective centroids. Also, with this configuration, translational motion is added to drive the magnetic micro particles towards the permanent magnet. The direction of this translational motion produced by the permanent magnet 27a is also opposite to that produced by the permanent magnet 27b. Similar phenomena take place when the reaction container 1 is moved from the position facing the permanent magnet 27b to a position facing the permanent magnet 27c, and this is repeated to magnetically swing the magnetic micro particles to form flocks.

Afterward, the reaction container 1 is transported to a position corresponding to the position F in FIG. 2, where magnetic micro particle flocks are magnetically adsorbed and separated from the liquid phase.

It should be noted that the permanent magnet 27h disposed at the most downstream position may also be used to serve as a magnet for the adsorption and separation of the magnetic micro particle flocks. In this case, the magnetic adsorption of magnetic micro particle flocks can be achieved by stopping the reaction line for a time period required for the adsorption.

Figure 7:
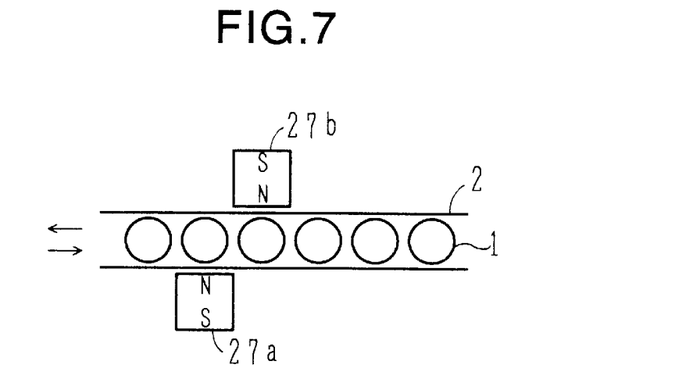
FIG. 7 is a diagram illustrating a modification to the embodiment shown in FIG. 6.

While in the embodiment of FIG. 6, the reaction containers 1 are transported in one direction, the holder 2 may be driven in the forward and backward directions. In this case, as shown in FIG. 7, only a pair of permanent magnets 27a, 27b may be disposed on one and the other sides of the holder 2 at different positions with the same pole (N-pole) directed to the reaction containers 1. Also in this configuration, magnetic micro particles are applied with temporally varying magnetic fields, similarly to the configuration of FIG. 6, to magnetically swing the magnetic micro particles to form flocks.

Incidentally, in the embodiments shown in FIGS. 6 and 7, if the reaction container holder 2 passes a route forming a closed loop and the reaction developed in the reaction container 1 requires a so long time period that the holder 2 must make two or more rounds of the loop, the reaction container 1, in which a reaction is in progress, inevitably passes through the illustrated region in which the permanent magnets are disposed. In this event, if the permanent magnets disposed along the route of the reaction container 1 interfere with the reaction, shielding plates made of a magnetic material such as permalloy or the like may be provided between the reaction container holder 2 and the permanent magnets 27a, 27c, 27e, 27g and between the reaction container holder 2 and the permanent magnets 27b, 27d, 27f, 27h such that these shielding plates are lowered when the reaction container 1 passes between these permanent magnets to magnetically shield the permanent magnets.

Next, a third embodiment of the present invention will be described with reference to FIG. 8. This embodiment utilizes a single mechanically movable magnet for applying varying magnetic fields to cause repetitive magnetical displacement of magnetic micro particles as well as for adsorbing flocks of magnetic micro particles for recovery.

Figure 8:
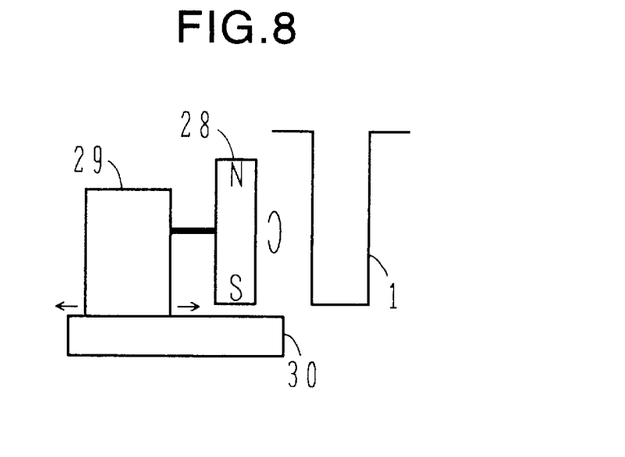
FIG. 8 is a diagram illustrating the configuration for applying a magnetic field according to a third embodiment of the present invention.

Referring specifically to FIG. 8, a permanent magnet 28 is arranged for rotation by a permanent magnet rotating mechanism 29 such as a motor or the like. The permanent magnet rotating mechanism 29 in turn is driven by a permanent magnet shifting mechanism 30 so as to shift the permanent magnet 28 toward and away from a reaction container 1. The rotation of the permanent magnet 28 causes the magnetic poles of the permanent magnet 28 to periodically move, so that a temporally varying magnetic field is applied to magnetic micro particles in the reaction container 1, with the result that flocks of the magnetic micro particles are produced. If the rotation of the permanent magnet 28 is temporarily stopped and the permanent magnet 28 is brought closer to the reaction container 1 by the shifting mechanism 30, the flocks of the magnetic micro particles are fixed.

Figure 9:
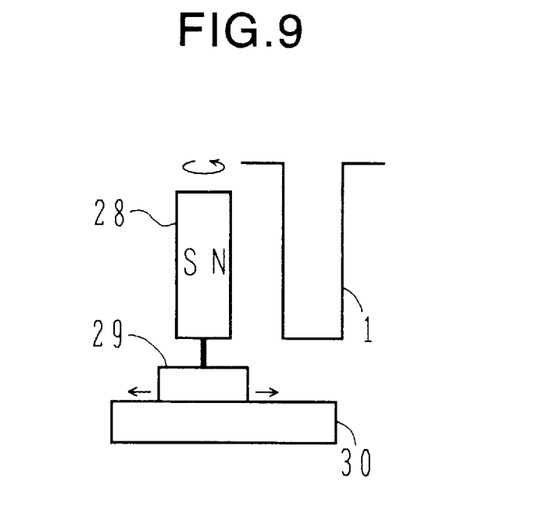
FIG. 9 is a diagram illustrating a modification to the embodiment shown in FIG. 8.

In the embodiment of FIG. 8, the rotating axis of the rotating mechanism 29 is directed in the horizontal direction to rotate the permanent magnet 28 thereabout. Alternatively, as shown in FIG. 9, the rotating axis of the rotating mechanism 29 may be directed in the vertical direction to rotate the permanent magnet 28 thereabout. Also with the configuration of FIG. 9, magnetic micro particles are applied with a temporally varying magnetic field, similarly to that of FIG. 8, so that magnetic micro particles are formed into flocks.

Next, a fourth embodiment of the present invention will be described with reference to FIG. 10. The foregoing embodiments have described examples of applying the present invention to a discrete type apparatus, whereas the fourth embodiment deals with a flow type apparatus.

Figure 10:
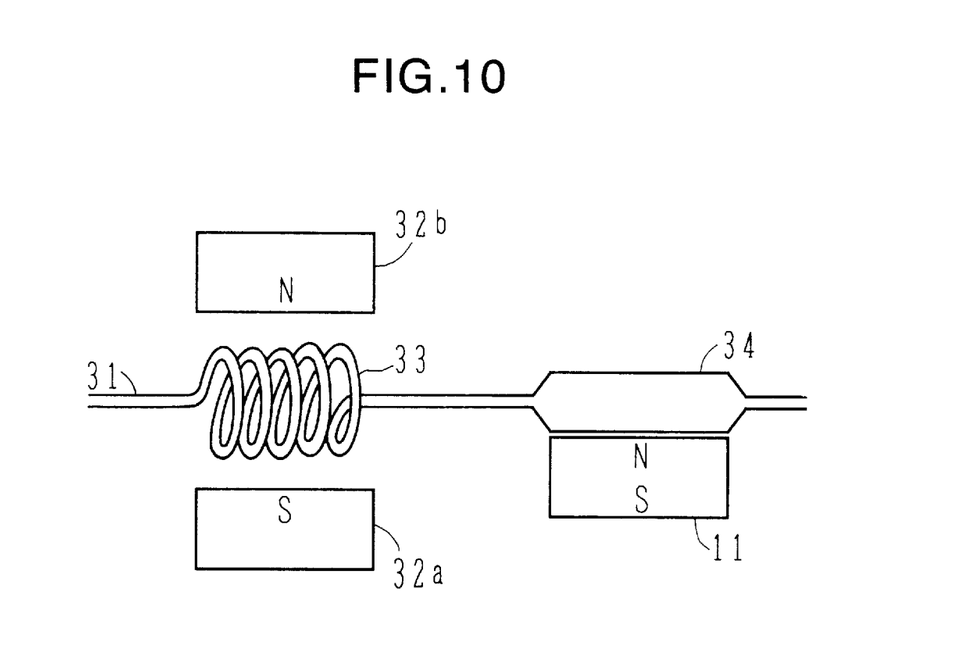
FIG. 10 is a diagram showing the configuration of a fourth embodiment of the present invention.

Referring specifically to FIG. 10, a conduit 31 through which a liquid including magnetic micro particles flows is formed with a coil portion 33, and two permanent magnets 32a, 32b for flocculation are disposed on one and the other sides of the coil portion 33 such that different poles thereof are opposite to each other. Also, a cell 34 is formed at a location downstream of the coil portion 33, and a permanent magnet 11 is disposed adjacent to this cell 34.

When the liquid including the magnetic micro particles spirally flows through the coil portion 33, the magnetic micro particles are applied with a temporally varying magnetic field generated by the permanent magnets 32a, 32b, so that the magnetic micro particles are repetitively displaced by the applied magnetic field and consequently flocculated with each other. The flocculated magnetic micro particles, i.e., flocks further flow to the cell 34 and are adsorbed by the permanent magnet 11.

In the embodiment of FIG. 10, as a liquid including magnetic micro particles spirally flows through the coil portion 33 formed in the middle of the conduit 31, the magnetic micro particles are subjected to a temporally varying magnetic field. In the alternative, the conduit may be formed with a portion in which a liquid including magnetic micro particles is prohibited from flowing, and electromagnets such as those used in the embodiment shown in FIG. 1 may be utilized to change the direction and intensity of a magnetic field at this portion. For modifying the configuration of FIG. 10 to this alternative, the coil portion 33 may be replaced with a cell such as the cell 34, and an electromagnet such as the horizontal coil 9 in FIG. 2 may be disposed instead of the permanent magnets 32a, 32b.

What is claimed is:

1. A method of separating magnetic particles on which an immunocomplex is bound, from a liquid phase in a container, comprising the steps of:

applying a varying magnetic field to said magnetic particles having the immunocomplex to cause said magnetic particles to be flocculated;

applying a static magnetic field to said container, in which flocculation has occurred, for magnetically fixing said magnetic particles on an inner wall of said container;

removing the liquid phase in said container while said magnetic particles are magnetically fixed on said inner wall of said container;

releasing said magnetic particles from said static magnetic field;

feeding a washing liquid into said container to suspend said magnetic particles in said washing liquid;

applying a varying magnetic field to said magnetic particles suspended in said washing liquid to cause said magnetic particles to be flocculated;

magnetically fixing said magnetic particles on said inner wall of said container by applying a static magnetic field to said washing liquid in which flocculation has occurred; and removing said liquid phase in said container while said magnetic particles are magnetically fixed on said inner wall of said container.

2. A separating method according to claim 1, wherein said varying magnetic field has an intensity that does not cause the solid supports to be magnetically fixed on the inner wall surface of said container.

3. A separating method according to claim 1, further comprising the step of adding a flocculent in said container for promoting flocculation prior to the step of applying the varying magnetic field.

4. A separating method according to claim 3, wherein said flocculent includes magnetic particles having a diameter in the range of 10–50 $\mu$m, and said magnetic particles on which an immunocomplex is bound have a diameter in the range of 1–2 $\mu$m.

5. An apparatus for separating magnetic particles on which an immunocomplex is bound, from a liquid phase in a container, comprising:

means for moving said container through a B-F (Bound-Free) separation station, a washing station and a photometric station;

means for applying an alternate current magnetic field to said container to cause said magnetic particles to flocculate;

means for applying a static magnetic field to said container in which the magnetic particles have been flocculated, whereby said magnetic particles are magnetically fixed onto an inner wall of said container; and means for removing said liquid phase from said container while said magnetic particles are magnetically fixed on said inner wall of said container.

6. A separating apparatus according to claim 5, wherein said means for applying said static magnetic field includes a permanent magnet.

7. A separating apparatus according to claim 5, further comprising means for feeding said container with a flocculent prior to applying said alternate current magnetic field.

8. A separating apparatus according to claim 5, further comprising means for feeding said container with a washing liquid after the liquid phase has been removed from said container.

* * * * *